United States Patent

Boller et al.

[11] 4,066,570
[45] Jan. 3, 1978

[54] PHENYL-PYRIMIDINES

[75] Inventors: Arthur Boller, Binningen; Marco Cereghetti, Basel; Hanspeter Scherrer, Therwil, all of Switzerland

[73] Assignee: Hoffman-La Roche Inc., Nutley, N.J.

[21] Appl. No.: 721,257

[22] Filed: Sept. 8, 1976

Related U.S. Application Data

[62] Division of Ser. No. 624,354, Oct. 21, 1975, Pat. No. 3,997,536.

[30] Foreign Application Priority Data

Oct. 25, 1974 Switzerland .................. 14313/74

[51] Int. Cl.² .............................. G02F 1/13; C09K 3/34
[52] U.S. Cl. ........................... 252/299; 252/408; 350/150; 350/160 LC
[58] Field of Search .................. 252/299, 408; 350/160 LC, 150

[56] References Cited

U.S. PATENT DOCUMENTS

| 3,923,857 | 12/1975 | Boller et al. ........................ 252/299 |
| 3,927,064 | 12/1975 | Boller et al. ........................ 252/299 |
| 3,927,066 | 12/1975 | Scherrer et al. ..................... 252/299 |
| 3,947,375 | 3/1976 | Gray et al. .......................... 252/299 |
| 3,952,046 | 4/1976 | Scherrer et al. ..................... 252/299 |
| 3,954,653 | 5/1976 | Yamazaki ............................ 252/299 |

FOREIGN PATENT DOCUMENTS

| 2,252,132 | 6/1975 | France ............................... 252/299 |
| 2,257,588 | 6/1973 | Germany ............................ 252/299 |
| 2,502,904 | 7/1975 | Germany ............................ 252/299 |
| 50-23385 | 3/1975 | Japan .................................. 252/299 |

OTHER PUBLICATIONS

Usol'Tseva, V. A. et al., Russ. Chem. Rev., vol. 32, No. 9, pp. 495-507 (Sept. 1963).
Gray, G. W. et al., Liquid Crystals & Plastic Crystals, vol. 1, John Wiley & Sons, Inc., pp. 103-142 (Jan. 1974).

*Primary Examiner*—Benjamin R. Padgett
*Assistant Examiner*—T. S. Gron
*Attorney, Agent, or Firm*—Samuel L. Welt; George M. Gould; William G. Isgro

[57] ABSTRACT

Phenyl-pyrimidines of the formula

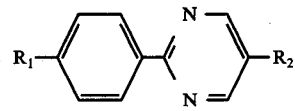

wherein $R_1$ and $R_2$ are as hereinafter set forth, are described. The end products are useful as liquid crystals.

25 Claims, No Drawings

PHENYL-PYRIMIDINES

This is a division, of application Ser. No. 624,354 filed Oct. 21, 1975, now U.S. Pat. No. 3,997,536.

BRIEF SUMMARY OF THE INVENTION

The invention relates to compounds of the formula

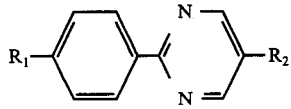
I wherein one of $R_1$ and $R_2$ is cyano and the other is straight-chain alkyl of 3 to 9 carbon atoms, straight-chain alkoxy of 2 to 9 carbon atoms or straight-chain alkanoyloxy of 2 to 9 carbon atoms.

In another aspect, the invention relates to nematic mixtures comprising the compounds of formula I alone or in combination with other nematic or non-nematic substances. In yet another aspect, the invention relates to an electro-optical apparatus comprising the phenyl-pyrimidines of formula I.

DETAILED DESCRIPTION OF THE INVENTION

The invention relates to compounds of the formula

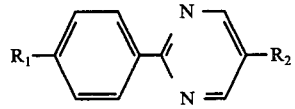
I wherein one of $R_1$ and $R_2$ is cyano and the other is straight-chain alkyl of 3 to 9 carbon atoms, straight-chain alkoxy of 2 to 9 carbon atoms or straight-chain alkanoyloxy of 2 to 9 carbon atoms.

The compounds of formula I of the invention are especially valuable and useful as components of liquid crystalline mixtures and, for the major part, themselves possess liquid crystalline properties, particularly nematic properties. The compounds of the invention possess inter alia a very high positive anisotropy of the dielectric constants ($\epsilon_{\parallel} > \epsilon_{\perp}$, wherein $\epsilon_{\parallel}$ is the dielectric constant along the longitudinal molecular axis and $\epsilon_{\perp}$ is the dielectric constant perpendicular thereto).

In an electric field, the compounds of formula I of the invention orientate themselves (because $\epsilon_{\parallel} > \epsilon_{\perp}$) with the direction of their largest dielectric constant, i.e., with their longitudinal axes parallel to the field direction. This effect is utilized, inter alia, in the interaction between embedded molecules and the liquid crystalline molecules (guest-host interaction) described by J. H. Heilmeier and L. A. Zanoni [Applied Physics Letters 13, 91 (1968)]. Another interesting application of the dielectric field orientation is found in the rotation cell discovered by M. Schadt and W. Helfrich [Applied Physics Letters 18, (1971)] as well as in the Kerr cell described in Molecular Crystals and Liquid Crystals 17, 355 (1972).

The electro-optical rotation cell is essentially a condenser having transparent electrodes, whose dielectric is formed from a nematic substance with $\epsilon_{\parallel} > \epsilon_{\perp}$. The longitudinal axes of the molecules of the liquid crystal are arranged in a twisted form between the condenser plates in the fieldless state, the twisting structure being defined by the given wall orientation of the molecules. After application of an electric potential to the condenser plates, the molecules adjust themselves with their longitudinal axes in the field direction, that is, perpendicular to the surface of the plates, by which means linear polarized light is no longer rotated in the dielectric, that is, the liquid crystal is uniaxially perpendicular to the surface of the plates. This effect is reversible and can be used in addition to control electrically the optical transmissivity of the condenser. A cell of this type is hereinafter referred to as a "rotation cell."

In such a "rotation cell," it is desirable to utilize compounds or mixtures which possess a low threshold. A low threshold is of considerable advantage for applications in which a small volume and a low energy requirement is of particular importance, for example, when a rotation cell is used in watches, pocket calculators, or the like.

It has now been found that the compounds of formula I of the invention possess a particularly low threshold. Moreover, they possess not only the necessary large positive anisotropy of the dielectric constants and a low threshold, but show slight viscosity, high response rate and a high stability, especially in the form of their mixtures with one another or with other nematic or non-nematic substances. The operation of electro-optical devices is accordingly possible with a lower voltage, shorter response time and, because of their high stability, with easier handling. An additional advantage exhibited by the compounds of the invention with nematic properties resides in the fact that they form colorless nematic phases.

The following are exemplary of the compounds of the invention;

5-n-propyl-2-(4-cyanophenyl)-pyrimidine;
5-n-butyl-2-(4-cyanophenyl)-pyrimidine;
5-n-pentyl-2-(4-cyanophenyl)-pyrimidine;
5-n-hexyl-2-(4-cyanophenyl)-pyrimidine;
5-n-heptyl-2-(4-cyanophenyl)-pyrimidine;
5-n-octyl-2-(4-cyanophenyl)-pyrimidine;
5-n-nonyl-2-(4-cyanophenyl)-pyrimidine;
5-ethoxy-2-(4-cyanophenyl)-pyrimidine;
5-n-propyloxy-2-(4-cyanophenyl)-pyrimidine;
5-n-butyloxy-2-(4-cyanophenyl)-pyrimidine;
5-n-pentyloxy-2-(4-cyanophenyl)-pyrimidine;
5-n-hexyloxy-2-(4-cyanophenyl)-pyrimidine;
5-n-heptyloxy-2-(4-cyanophenyl)-pyrimidine;
5-n-octyloxy-2-(4-cyanophenyl)-pyrimidine;
5-n-nonyloxy-2-(4-cyanophenyl)-pyrimidine;
5-acetoxy-2-(4-cyanophenyl)-pyrimidine;
5-n-propionyloxy-2-(4-cyanophenyl)-pyrimidine;
5-n-butyryloxy-2-(4-cyanophenyl)-pyrimidine;
5-n-valeryloxy-2-(4-cyanophenyl)-pyrimidine;
5-n-hexanoyloxy-2-(4-cyanophenyl)-pyrimidine;
5-n-heptanoyloxy-2-(4-cyanophenyl)-pyrimidine;
5-n-octanoyloxy-2-(4-cyanophenyl)-pyrimidine;
5-n-nonanoyloxy-2-(4-cyanophenyl)-pyrimidine;
5-cyano-2-(4-n-propylphenyl)-pyrimidine;
5-cyano-2-(4-n-butylphenyl)-pyrimidine;
5-cyano-2-(4-n-pentylphenyl)-pyrimidine;
5-cyano-2-(4-n-hexylphenyl)-pyrimidine;
5-cyano-2-(4-n-heptylphenyl)-pyrimidine;
5-cyano-2-(4-n-octylphenyl)-pyrimidine;
5-cyano-2-(4-n-nonylphenyl)-pyrimidine;
5-cyano-2-(4-ethoxypheny)-pyrimidine;
5-cyano-2-(4-n-propyloxyphenyl)-pyrimidine;
5-cyano-2-(4-n-butyloxyphenyl)-pyrimidine;
5-cyano-2-(4-n-pentyloxyphenyl)-pyrimidine;
5-cyano-2-(4-n-hexyloxyphenyl)-pyrimidine;

5-cyano-2-(4-n-heptyloxyphenyl)-pyrimidine;
5-cyano-2-(4-n-octyloxyphenyl)-pyrimidine;
5-cyano-2-(4-n-nonyloxyphenyl)-pyrimidine;
5-cyano-2-(4-acetoxyphenyl)-pyrimidine;
5-cyano-2-(4-n-propionyloxyphenyl)-pyrimidine;
5-cyano-2-(4-n-butyryloxyphenyl)-pyrimidine;
5-cyano-2-(4-n-valeryloxyphenyl)-pyrimidine;
5-cyano-2-(4-n-hexanoyloxyphenyl)-pyrimidine;
5-cyano-2-(4-n-heptanoyloxyphenyl)-pyrimidine;
5-cyano-2-(4-n-octanoyloxyphenyl)-pyrimidine;
5-cyano-2-(4-n-nonanoyloxyphenyl)-pyrimidine;

Among the preferred phenyl-pyrimidines of formula I are those in which one of $R_1$ and $R_2$ is cyano and the other is a straight-chain alkyl group containing 5 to 7 carbon atoms or a straight-chain alkoxy group containing 4 to 6 carbon atoms. Most preferred are:
5-n-heptyl-2-(4-cyanophenyl)-pyrimidine,
5-n-pentyl-2-(4-cyanophenyl)-pyrimidine,
5-cyano-2-(4-n-pentylphenyl)-pyrimidine,
5-cyano-2-(4-n-hexylphenyl)-pyrimidine,
5-cyano-2-(4-n-butyloxyphenyl)-pyrimidine and
5-cyano-2-(4-n-pentyloxyphenyl)-pyrimidine.

The phenyl-pyrimidines of formula I can be prepared by a. dehydrating a compound of the formula

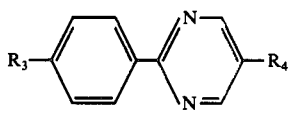

wherein one of $R_3$ and $R_4$ is a straight-chain alkyl containing 3 to 9 carbon atoms, straight-chain alkoxy containing 2 to 9 carbon atoms or straight-chain alkanoyloxy containing 2 to 9 carbon atoms and the other is aminocarbonyl, or b. to prepare phenyl-pyrimidines of formula I wherein $R_1$ is cyano and $R_2$ is straight-chain alkyl containing 3 to 9 carbon atoms, straight-chain alkoxy containing 2 to 9 carbon atoms or straight-chain alkanoyloxy containing 2 to 9 carbon atoms, reacting a compound of the formula

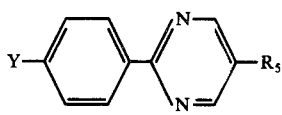

wherein $R_5$ is straight-chain alky containing 3 to 9 carbon atoms, straight-chain alkoxy containing 2 to 9 carbon atoms or straight-chain alkanoyloxy containing 2 to 9 carbon atoms and Y is halogen or arylsulfonyloxy,
with copper (I) cyanide or sodium cyanide, or c. to prepare phenyl-pyrimidines of formula I wherein $R_1$ is cyano and $R_2$ is straight-chain alkyl containing 3 to 9 carbon atoms, straight-chain alkoxy containing 2 to 9 carbon atoms or straight-chain alkanoyloxy containing 2 to 9 carbon atoms, dehydrating a compound of the formula

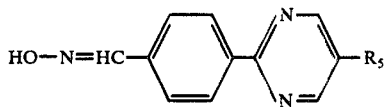

wherein $R_5$ is as herein described, or d. to prepare phenyl-pyrimidines of formula I wherein $R_1$ is straight-chain alkyl containing 3 to 9 carbon atoms, straight-chain alkoxy containing 2 to 9 carbon atoms or straight-chain alkanoyloxy containing 2 to 9 carbon atoms and $R_2$ is cyano, reductively dehalogenating a compound of the formula

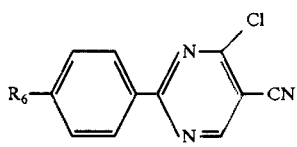

wherein $R_6$ is straight-chain alkyl containing 3 to 9 carbon atoms, straight-chain alkoxy containing 2 to 9 carbon atoms or straight-chain alkanoyloxy containing 2 to 9 carbon atoms, or e. to prepare phenyl-pyrimidines of formula I wherein $R_1$ is straight-chain alkyl containing 3 to 9 carbon atoms, straight-chain alkoxy containing 2 to 9 carbon atoms or straight-chain alkanoyloxy containing 2 to 9 carbon atoms and $R_2$ is cyano, reacting a compound of the formula

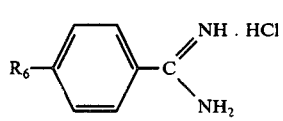

wherein $R_6$ is as herein described, with an alkali salt of acetalized hydroxymethylene-cyanacetaldehydd.

In process aspect (a), a compound of formula II is dehydrated. This dehydration can be carried out utilizing any suitable dehydrating agent such as phosphorus oxychloride, phosphorus pentoxide, thionyl chloride or acetic anhydride. Further, the dehydration can be carried out in an inert organic solvent, such as, a hydrocarbon or halogenated hydrocarbon, if desired, in the presence of a base such as sodium acetate, pyridine or triethanolamine. However, the dehydration can also be carried out in the absence of an inert organic solvent. The dehydration is carried out at the reflux temperature of the mixture. The pressure at which the dehydration is carried out is not critical; it is, however, advantageous to carry out the dehydration at atmospheric pressure.

In process aspect (b), a compound of formula III is reacted with copper (I) cyanide or sodium cyanide. This reaction is conveniently carried out in an inert organic solvent, such as, ethyleneglycol, tetrahydrofuran, dimethylformamide, dimethylsulfoxide, pyridine or acetonitrile. The temperature and pressure at which the reaction is carried out are not critical; it is convenient, however, to carry out the reaction at atmospheric pressure and at a temperature in the range of from about room temperature to about the reflux temperature of the mixture. In the compound of formula III, Y is preferably halogen, especially bromine.

In process aspect (c), a compound of formula IV is dehydrated. This dehydration is conveniently carried out using acetic anhydride or with anhydrous sodium acetate in glacial acetic acid. Further, the dehydration is carried out at the reflux temperature of the mixture. The pressure at which the reaction is carried out is not critical; it is advantageous, however, to carry out the dehydration at atmospheric pressure.

In process aspect (d), a compound of formula V is reductively dehalogenated. This dehalogenation is advantageously carried out using zinc dust in a mixture of dioxane and water. The dehalogenation preferably takes place at the reflux temperature of the dehalogenation mixture. The pressure at which the dehalogenation is carried out is not cricital; it is advantageous, however, to carry out the dehalogenation at atmospheric pressure.

In process aspect (e), a compound of formula VI is reacted with an alkali salt of acetalized hydroxymethylene-cyanacetaldehyde. An aqueous solution of the compound of formula VI is utilized and, after reaction, the mixture is made slightly acidic. The resulting mixture is then evaporated and the residue treated with acetic anhydride. The reaction is preferably carried out at a temperature in the range of from about room temperature to about 100° C. The pressure at which the reaction is carried out is not critical; atmospheric pressure is preferred.

The preparation of the starting materials of formulas II, III, IV, V and VI, in which one of the symbols $R_3$ and $R_4$ or $R_5$ and $R_6$ is straight-chain alkyl containing 3 to 9 carbon atoms, is illustrated in Formula Schemes A to E hereinafter. In these Formula Schemes, the term "alkyl" represents straight-chain alkyl containing 3 to 9 carbon atoms. Similar reactions as set forth in Formula Schemes A to E can be used for the preparation of the starting materials of formulas II, III, IV, V and VI, in which one of the symbols $R_3$ and $R_4$ or $R_5$ and $R_6$ is straight-chain alkoxy containing 2 to 9 carbon atoms or straight-chain alkanoyloxy containing 2 to 9 carbon atoms.

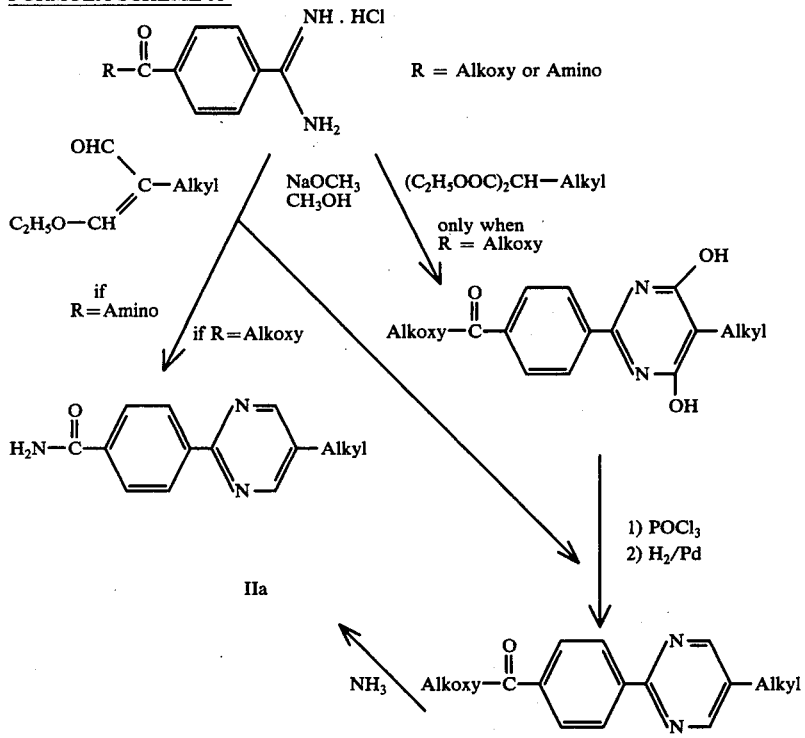

FORMULA SCHEME A

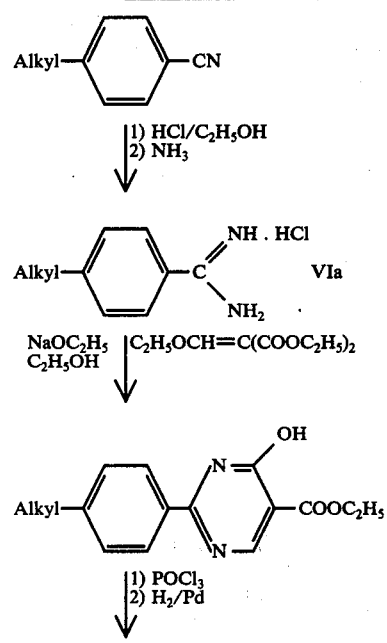

FORMULA SCHEME B

-continued
FORMULA SCHEME B

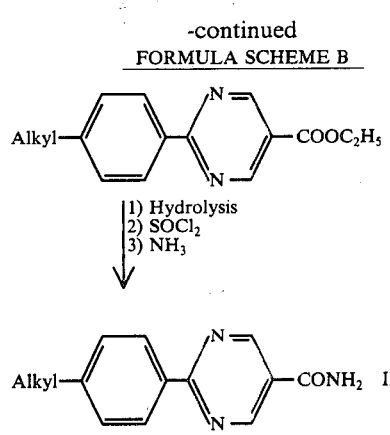

1) Hydrolysis
2) SOCl₂
3) NH₃

FORMULA SCHEME C

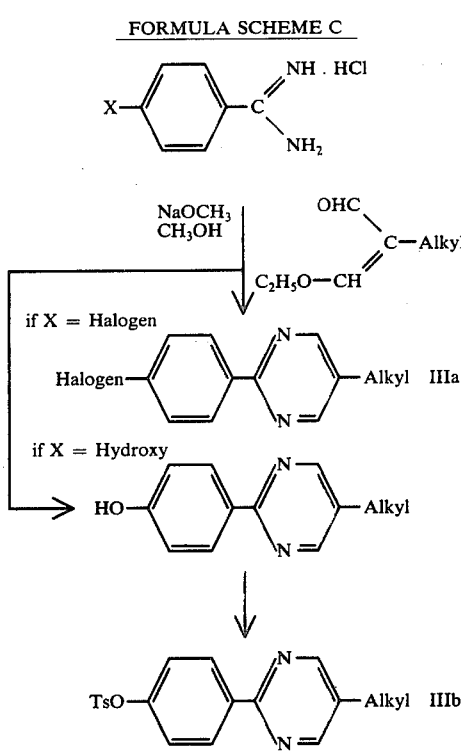

FORMULA SCHEME D

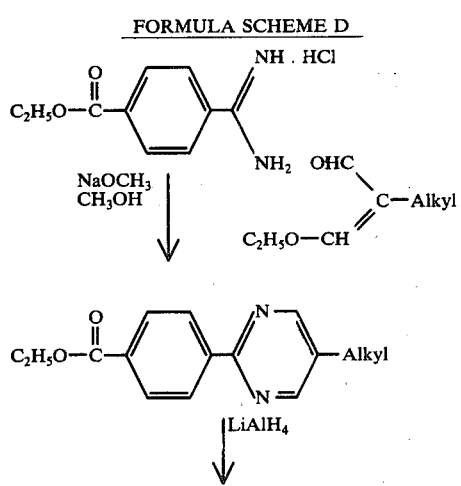

-continued
FORMULA SCHEME D

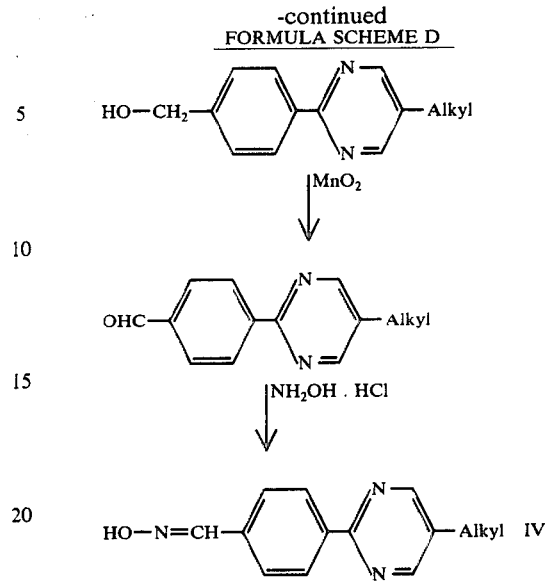

FORMULA SCHEME E

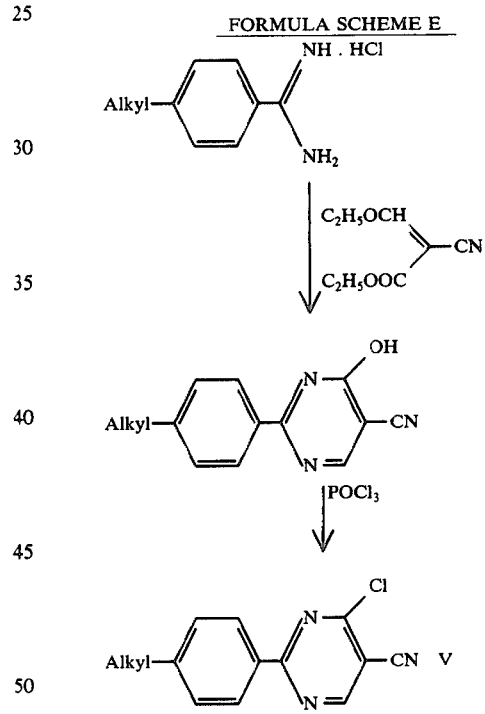

The physical properties of some of the phenyl-pyrimidines of formula I are given in the following Table:

| $R_1$ | $R_2$ | Melting point | Clearing point |
|---|---|---|---|
| CN | n-Pentyl | 69.4°–70.8° C | (51.9° C)* |
| CN | n-Hexyl | 53.5°–54.5° C | (35.5°–36.5° C)* |
| CN | n-Heptyl | 44.2°–44.7° C | 50.1°–50.4° C |
| CN | n-Octyl | 66.1°–66.8° C | (47.1° C)* |
| n-Propyl | CN | 125.9°–126.0° C | (106.4° C)* |
| n-Butyl | CN | 108.6°–109.5° C | (101.5° C)* |
| n-Pentyl | CN | 96.0°–96.2° C | 109.0° C |
| n-Hexyl | CN | 86.3°–87.8° C | 102.6°–103.2° C$^{a)}$ |
| n-Heptyl | CN | 96.3° C | 109.0° C$^{b)}$ |
| Ethoxy | CN | 152.6°–153.0° C | (149.7° C)* |
| n-Propyloxy | CN | 146.2°–146.6° C | (137.0° C)* |
| n-Butyloxy | CN | 119.1°–120.0° C | 139.3° C |
| n-Pentyloxy | CN | 98.0°–98.1° C | 133.2° C$^{c)}$ |
| n-Hexyloxy | CN | 93.5°–93.8° C | 134.0° C$^{d)}$ |

-continued

| $R_1$ | $R_2$ | Melting point | Clearing point |
|---|---|---|---|
| n-Heptyloxy | CN | 102.4° C | 129.5° C[e] |

*monotropic clearing point
[a]smectic up to 101.3° C
[b]whole liquid crystalline range is smectic
[c]smectic up to 102.1° C
[d]smectic up to 121.2° C
[e]smectic up to 126.9° C The phenyl-pyrimidines of formula I can be used in the form of mixtures with one another, mixtures which correspond to a eutectic being especially preferred.

The phenyl-pyrimidines of formula I are preferably used in the form of mixtures with other nematic or non-nematic substances such as, for example, with compounds of the formula

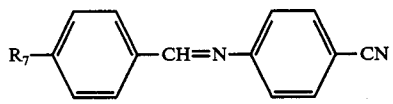

VIII wherein $R_7$ is straight-chain alkyl containing 2 to 8 carbon atoms, straight-chain alkoxy containing 4 to 7 carbon atoms, straight-chain alkanoyloxy containing 2 to 8 carbon atoms or straight-chain alkylcarbonate containing 2 to 11 carbon atoms.
or with compound of the formula

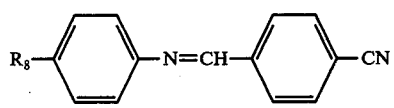

IX wherein $R_8$ is straight-chain alkyl containing 4 to 7 carbon atoms or straight-chain alkylcarbonate containing 2 to 11 carbon atoms,
or with compounds of the formula

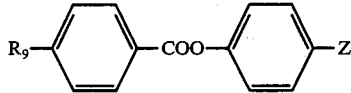

X wherein Z is cyano, straight-chain alkyl containing 1 to 9 carbon atoms, straight-chain alkoxy containing 1 to 9 carbon atoms or straight-chain alkanoyloxy containing
1 to 10 carbon atoms and $R_9$ is straight-chain alkyl containing
4 to 8 carbon atoms, straight-chain alkoxy containing 5 to 8
carbon atoms, straight-chain alkanoyloxy containing 2 to 8
carbon atoms or straight-chain alkylcarbonate containing
3 to 11 carbon atoms,
or with compounds of the formula

XI wherein $R_{10}$ is straight-chain alkyl containing 5 to 7 carbon atoms, straight-chain alkoxy containing 5 to 7 carbon atoms, straight-chain alkanoyloxy containing 4 to 9 carbon atoms or straight-chain alkylcarbonate containing 4 to 11 carbon atoms,
or with trans-cinnamic acid esters of the formula

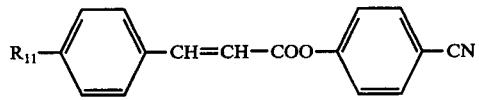

XII wherein $R_{11}$ is straight-chain alkyl containing 1 to 8 carbon atoms;
or with compounds of the formula

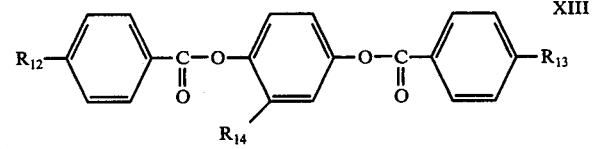

XIII wherein $R_{12}$ and $R_{13}$ each are straight-chain alkyl containing 1 to 10 carbon atoms, straight-chain alkoxy containing 1 to 10 carbon atoms, straight-chain alkanoyloxy containing 2 to 11 carbon atoms or straight-chain alkylcarbonate containing 2 to 11 carbon atoms and $R_{14}$ is chlorine or bromine, or methyl, acetyl or methoxycarbonyl.

The compounds of formula VIII wherein $R_7$ is straight-chain alkylcarbonate containing 2 to 11 carbon atoms are novel and can be prepared by condensing a compound of the formula

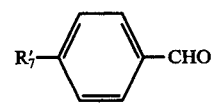

XIV wherein $R'_7$ is straight-chain alkylcarbonate containing 2 to 11 carbon atoms,
with p-aminobenzonitrile.

The compounds of formula IX wherein $R_8$ is straight-chain alkylcarbonate containing 2 to 11 carbon atoms are novel and can be prepared by condensing a compound of the formula

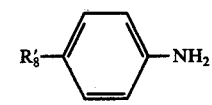

XV wherein $R'_8$ is straight-chain alkylcarbonate containing 2 to 11 carbon atoms,
with p-cyanobenzaldehyde.

The compounds of formula X wherein $R_9$ is straight-chain alkylcarbonate containing 3 to 11 carbon atoms and Z is cyano are novel and can be prepared by reacting a compound of the formula

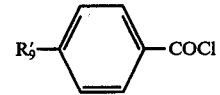

XVI wherein $R'_9$ is straight-chain alkylcarbonate containing 3 to 11 carbon atoms,
with p-hydroxybenzonitrile.

The compounds of formula XI wherein $R_{10}$ is straight-chain alkanoyloxy containing 4 to 9 carbon atoms or straight-chain alkylcarbonate containing 4 to 11 carbon atoms are novel and can be prepared by reacting a compound of the formula $$R'_{10}COCl \qquad XVII$$

wherein $R'_{10}$ is straight-chain alkyl containing 3 to 8 carbon atoms or straight-chain alkoxy containing 3 to 10 carbon atoms,
with 4'-cyano-4-hydroxy-biphenyl.

The trans-cinnamic acid esters of formula XII are novel and can be prepared by reacting a compound of the formula

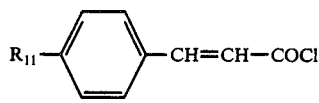

wherein $R_{11}$ is as herein described,
with p-hydroxybenzonitrile.

The phenyl-pyrimidines of formula I can be present in nematic mixtures for electro-optical purposes in any weight ratio or, as already mentioned, can even be used individually in nematic form for electro-optical purposes. The proportion of a phenyl-pyrimidine of formula I in a nematic mixture usually is in the range of from about 5 to about 95 weight percent and preferably in the range of from about 25 to about 75 weight percent.

The following mixtures are especially preferred:

5-n-Pentyl-2-(4-cyanophenyl)-pyrimidine and 5-n-hexyl-2-(4-cyanophenyl)-pyrimidine in a molar ratio of 1:1; melting point 38.5° C; clearing point 43° C.

5-n-Pentyl-2-(4-cyanophenyl)-pyrimidine, p-n-hexylbenzoic acid p'-cyanophenyl ester and p-n-octylbenzoic acid p'-cyanophenyl ester in a molar ratio of 1:1:1; melting point 15°–18° C; clearing point 52.3° C.

5-n-Hexyl-2-(4-cyanophenyl)-pyrimidine, p-n-hexylbenzoic acid p'-cyanophenyl ester and p-n-octylbenzoic acid p'-cyanophenyl ester in a molar ratio of 1:1:1; melting point 14°–17° C; clearing point 52.3° C.

5-n-Pentyl-2-(4-cyanophenyl)-pyrimidine, p-n-heptylbenzoic acid p'-cyanophenyl ester and p-n-octylbenzoic acid p'-cyanophenyl ester in a molar ratio of 1:1:1; melting point 23.7° C; clearing point 55.5° C.

5-n-Pentyl-2-(4-cyanophenyl)-pyrimidine, 4'-n-heptyl-4-cyanobiphenyl and 4'-n-pentyl-4-cyanobiphenyl in a molar ratio of 1:1:1; melting point 20° C; clearing point 42.3° C.

5-n-Hexyl-2-(4-cyanophenyl)-pyrimidine, 4'-n-heptyl-4-cyanobiphenyl and 4'-n-pentyl-4-cyanobiphenyl in a molar of 1:1:1; melting point 19°–21° C; clearing point 39°–40° C.

5-n-Pentyl-2-(4-cyanophenyl)-pyrimidine and 5-n-heptyl-2-(4-cyanophenyl)-pyrimidine in a molar ratio of 1:1; melting point 25°–29° C; clearing point 49.2° C.

5-n-Heptyl-2-(4-cyanophenyl)-pyrimidine, p-n-hexanoyloxy-benzoic acid p'-ethoxyphenyl ester, p-n-hexylbenzoic acid p'-cyanophenyl ester and p-n-octylbenzoic acid p'-cyanophenyl ester in a molar ratio of 1:1:1:1; melting point 20°–22° C; clearing point 52.2° C.

5-n-Heptyl-2-(4-cyanophenyl)-pyrimidine, p-n-hexylbenzoic acid p'-cyanophenyl ester, p-n-octylbenzoic acid p'-cyanophenyl ester and methylhydroquinone di(p-butylbenzoate) in a molar ratio of 1:1:1:1; melting point 20° C; clearing point 67.9° C.

5-n-Pentyl-2-(4-cyanophenyl)-pyrimidine, 5-n-heptyl-2-(4-cyanophenyl)-pyrimidine and p-n-heptylbenzoic acid p'-cyanophenyl ester in a molar ratio of 1:1:1; melting point 25°–28° C; clearing point 54.3° C.

5-n-Pentyl-2-(4-cyanophenyl)-pyrimidine, 5-n-heptyl-2-(4-cyanophenyl)-pyrimidine, p-n-heptylbenzoic acid p'-cyanophenyl ester and p-n-hexanoyloxybenzoic acid p'-ethoxyphenyl ester in a molar ratio of 1:1:1:1; melting point 14°–15° C; clearing point 55.7° C.

5-n-Heptyl-2-(4-cyanophenyl)pyrimidine, 5-n-pentyl-2-(4-cyanophenyl)-pyrimidine and 4'-heptyl-4-cyanobiphenyl in a molar of 1:1:1; melting point 14° C; clearing point 43.8° C.

63.4% of 4'-n-pentyl-4-cyanobiphenyl, 31.6% of 4'-heptyl-4-cyanobiphenyl and 5.0% of 5-cyano-2-(4-butyloxyphenyl)-pyrimidine; melting point <0° C; clearing point 42.7°–43.0° C.

63.4% of 4'-pentyl-4-cyanobiphenyl, 31.6% of 4'-heptyl-4-cyanobiphenyl and 5.0% of 5-cyano-2-(4-n-pentylphenyl)-pyrimidine; melting point < 0° C; clearing point 41.5°–41.7° C.

63.4% of 4'-n-pentyl-4-cyanobiphenyl, 31.6% of 4'-n-heptyl-4-cyanobiphenyl and 5.0% of 5-cyano-2-(4-n-pentyloxyphenyl)-pyrimidine; melting point <0° C; clearing point 42.5°–42.9° C.

60.0% of 4'-n-pentyl-4-cyanobiphenyl, 30.0% of 4'-n-heptyl-4-cyanobiphenyl and 10.0% of 5-cyano-2-(4-n-pentylphenyl)-pyrimidine; melting point <3° C; clearing point 45.2°–45.5° C.

63.4% of 4'-n-pentyl-4-cyanobiphenyl, 31.6% of 4'-n-heptyl-4-cyanobiphenyl and 5.0% of 5-cyano-2-(4-n-butylphenyl)-pyrimidine; melting point <3° C; clearing point 40.8° C.

63.4% of 4'-n-pentyl-4-cyanobiphenyl, 31.6% of 4'-n-heptyl-4-cyanobiphenyl and 5.0% of 5-cyano-2-(4-n-hexylphenyl)-pyrimidine; melting point < 3° C; clearing point 40.9°–41.1° C.

57.2% of 4'-n-pentyl-4-cyanobiphenyol, 28.6% of 4'-n-heptyl-4-cyanobiphenyl, 9.5% of 5-cyano-2-(4-n-pentylphenyl)-pyrimidine and 4.7% of 5-cyano-2-(4-n-hexylphenyl-pyrimidine; melting point <3° C; clearing point 47.7°–48.1° C.

56.8% of 4'-n-pentyl-4-cyanobiphenyl, 28.4% of 4'-n-heptyl-4-cyanobiphenyl, 9.5% of 5-cyano-2-(4-n-pentyloxyphenyl)-pyrimidine and 5.3% of 5-cyano-2-(4-n-hexylphenyl)-pyrimidine; melting point < 3° C; clearing point 50.0°–50.5° C.

54.0% of 4'-n-pentyl-4-cyanobiphenyl, 27.0% of 4'-n-heptyl-4-cyanobiphenyl, 5.0% of 5-cyano-2-(4-n-butylphenyl)-pyrimidine, 9.0% of 5-cyano-2-(4-n-pentylphenyl) pyrimidine and 5.0% of 5-cyano-2-(4-n-hexylphenyl-pyrimidine; melting point <3° C; clearing point 50.2°–50.7° C.

54.0% of 4'-n-pentyl-4-cyanobiphenyl, 27.0% of 4'-n-heptyl-4-cyanobiphenyl, 5.0% of 5-cyano-2-(4-n-butylphenyl)-pyrimidine, 5.0% of 5-cyano-2-(4-n-hexylphenyl)-pyrimidine and 9.0% of 5-cyano-2-(4-n-pentyloxyphenyl)-pyrimidine; melting point <3° C; clearing point 52.4°–53.0° C.

49.5% of 4'-n-pentyl-4-cyanobiphenyl, 13.5% of 4'-n-heptyl-4-cyanobiphenyl, 11.7% of 4'-n-heptyloxy-4-cyanobiphenyl, 15.3% of 4'-n-octyloxy-4-cyanobiphenyl, 5.0% of 5-cyano-2-(4-n-pentylphenyl)-pyrimidine and 5.0% of 5-cyano-2-(4-n-butyloxyphenyl)-pyrimidine; melting point <3° C; clearing point 61.1°–61.4° C.

53.4% of 4'-n-pentyl-4-cyanobiphenyl, 26.6% of 4'-n-heptyl-4-cyanobiphenyl, 5.0% of 5-cyano-2-(4-n-pentylphenyl)-pyrimidine, 5.0% of 5-cyano-2-(4-n-hexylphenyl)-pyrimidine, 5.0% of 5-cyano-2-(4-n-heptylphenyl)-pyrimidine and 5.0% of 5-cyano-2-(4-n-butyloxyphenyl)-pyrimidine; melting point <3° C; clearing point 53.4°–54.0° C.

12.2% of p-[(p-n-propylbenzylidene)amino]-benzonitrile, 32.8% of p-[(p-n-butylbenzylidene)amino]-benzonitrile, 44.4% of p-](p-n-hexylbenzylidene)amino]-benzonitrile, 1.3% of 5-cyano-2-(4-n-propylphenyl)-pyrimidine, 1.7% of 5-cyano-2-(4-n-butylphenyl)-pyrimidine, 2.2% of 5-cyano-2-(4-n-pentylphenyl)-pyrimidine, 3.4% of 5-cyano-2-(4-n-hexylphenyl)-pyrimidine and 2.0% of 5-cyano-2-(4-n-heptylphenyl)-pyrimidine; melting point <0° C; clearing point 67.6°–67.7° C.

The Examples which follow further illustrate the invention, for instance, the compounds of formula I as well as the compounds of formulas VIII to XII. All temperatures are given in degrees Centigrade, unless otherwise stated.

EXAMPLE 1

Preparation of 5-n-heptyl-2-(4-cyanophenyl)-pyrimidine 1.9 G. of 4-(4-n-heptylpyrimid-2-yl)benzoic acid amide are allowed to reflux with stirring for 80 minutes in a mixture of 40 ml. of ethylene chloride and 0.63 ml. of phosphorus oxychloride. The reaction mixture diluted with ether is washed with 2N sodium hydroxide, then with water to neutrality. After drying over sodium sulfate and evaporation of the organic phase, there is obtained 1.9 g. of 5-n-heptyl-2-(4-cyanophenyl)-pyrimidine which are distilled under high vacuum. M.P. 44.2°–44.7°; clearing point 50.1°–50.4°.

The starting material is prepared as follows:

0.07 Mol. of 2-n-heptyl-malono-tetraethylacetal are stirred in 35 ml. of ethanol with 0.14 mole of water and 2 drops of concentrated sulfuric acid at 50° under an atmosphere of nitrogen for 15 minutes. By shaking out the reaction mixture previously diluted with ether with aqueous sodium carbonate solution, the acidic 2-heptyl-malonaldehyde produced as a side-product can be separated from the neutral 2-n-heptyl-3-ethoxy-acrolein.

A suspension of 0.1 mole of 4-amidino-benzoic acid ethyl ester hydrochloride, 0.1 mole of 2-n-heptyl-3-ethoxy-acrolein and 0.14 mole of sodium ethylate in 100 ml. of methanol is stirred overnight at room temperature under an atmosphere of nitrogen. After the usual work up and separation into basic and acidic fractions, there is obtained 4(4-n-heptylpyrimid-2-yl)-benzoic acid ethyl ester and 4-(4-n-heptylpyrimid-2-yl)-benzoic acid.

A. 4.4 G. of 4-(4-n-heptylpyrimid-2-yl)-benzoic acid ethyl ester dissolved in 50 ml. of a methanol-dichloromethane (1:1) mixture are treated with 30 ml. of liquid ammonia in a laboratory autoclave and then heated to 90° for 5 hours (pressure: 16 atmospheres). The reaction mixture is evaporated to dryness and the poorly soluble amide separated from the unreacted educt, whereby there is obtained 4-(4-n-heptylpyrimid-2yl)-benzoic acid amide.

B 2.3 G. of 4-(4-n-heptylpyrimid-2-yl)benzoic acid and 1.9 ml. of thionyl chloride are allowed to reflux in 100 ml. of benzene for 8 hours and then the reaction mixture is evaporated to dryness on a vacuum film evaporator. The resulting residue is dissolved in 50 ml. of dichloromethane and then ammonia is led into the solution at room temperature for two hours, whereby there is obtained 4-(4-heptylpyrimid-2-yl)-benzoic acid amide in a practically quantitative yield.

In an analogous manner to that described above, the following compounds were prepared:
4-(4-n-butylpyrimid-2-yl)-benzoic acid amide,
4-(4-n-pentylpyrimid-2-yl)-benzoic acid amide, and
4-(4-n-octylpyrimid-2-yl)-benzoic acid amide.

EXAMPLE 2

Preparation of 5-n-butyl-2-(4-cyanophenyl)-pyrimidine 11.23 G. of 4-(4-n-butylpyrimid-2-yl)-benzoic acid amide are maintained at reflux for 90 minutes in a mixture of 250 ml. of ethylene chloride and 4.5 ml. of phosphorus oxychloride with stirring. The mixture, diluted with ether, is washed with 2-N sodium hydroxide and then with water until neutral. The organic phase is dried over sodium sulfate and evaporated to give 11.77 g. of 5-n-butyl-2-(4-cyanophenyl)-pyrimidine which are distilled in a high vacuum; melting point 60.9°–61.8° C.

EXAMPLE 3

Preparation of 5-n-pentyl-2-(4-cyanophenyl)-pyrimidine 0.8 G. of 4-(4-n-pentylpyrimid-2-yl)-benzoic acid amide are maintained at reflux for 80 minutes in a mixture of 20 ml. of ethylene chloride and 0.35 ml. of phosphorus oxychloride with stirring. The mixture, diluted with ether, is washed with 2-N sodium hydroxide and then with water until neutral. The organic phase is dried over sodium sulfate and evaporated to give 0.82 g. of 5-n-pentyl2-(4-cyanophenyl)-pyrimidine which are distilled in a high vacuum; melting point 69.4°–70.8° C; clearing point 51.9° C.

EXAMPLE 4

Preparation of 5-n-hexyl-2-(4-cyanophenyl)-pyrimidine 15.58 G. of 4-(4-n-hexylpyrimid-2-yl)-benzoic acid amide are maintained at reflux for 90 minutes in a mixture of 350 ml. of ethylene chloride and 5.58 ml. of phosphorus oxychloride with stirring. The mixture, diluted with ether, is washed with 2-N sodium hydroxide and then with water until neutral. The organic phase is dried over sodium sulfate and evaporated to give 14.6 g. of 5-n-hexyl2-(4-cyanophenyl)-pyrimidine which are distilled in a high vacuum; melting point 53.5°–54.5° C; clearing point 35.5°–36.5° C.

The starting material is prepared as follows:

0.1 mol. of 2-n-hexyl-malono-tetraethylacetal are stirred in 40 ml. of ethanol with 0.2 mol. of water and 3 drops of concentrated sulfuric acid at 50° C. under nitrogen for 18 hours. By shaking out the mixture, previously diluted with ether, with aqueous sodium carbonate solution, the acidic 2-hexyl-malonaldehyde produced as a by-product can be separated from the neutral 2-n-hexyl3-ethoxy-acrolein.

89 G. of 4-methylimido-benzoic acid methyl ester hydrochloride, suspended in 150 ml. of methanol, are treated at -40° C. with 60 ml. of liquid ammonia, added to a laboratory autoclave, pressurized to 30 atmospheres of nitrogen and held at 70° C. for 24 hours. The crystallized product is removed by filtration, washed with hexane and dried at 40° C. in vacuo (14 mm), whereby there are obtained 72 g. of 4-amidino-benzoic acid amide hydrochloride.

0.082 mol. of 4-amidino-benzoic acid amide hydrochloride, suspended in a solution of 0.082 mol. of 2-n-hexyl-3-ethoxy-acrolein and 0.14 mol. of sodium methylate in 150 ml. of methanol, are stirred overnight under an atmosphere of nitrogen at room temperature. The precipitate obtained by dilution of the mixture with 3 liters of ether is removed by filtration, washed with water until neutral and dried at 40° C. in a vacuum drying cupboard, whereby there are obtained 17.9 g. of 4-(4-n-hexylpyrimid-2-yl)-benzoic acid amide; melting point 231.6°–233.0° C.

EXAMPLE 5

Preparation of 5-n-octyl-2-(4-cyanophenyl)-pyrimidine 1.84 G. of 4-(4-n-octylpyrimid-2-yl)-benzoic acid amide are maintained at reflux for 80 minutes in a mixture of 40 ml. of ethylene chloride and 0.63 ml. of phosphorus oxychloride with stirring. The mixture, diluted with ether, is washed with 2-N sodium hydroxide and then with water until neutral. The organic phase is dried over sodium sulfate and evaporated to give 1.91 g. of 5-octyl-2-(4-cyanophenyl)-pyrimidine which are distilled in a high vacuum; melting point 66.1°–66.5° C; clearing point 47.5° C.

EXAMPLE 6

Preparation of 5-cyano-2-(4-n-propylphenyl)-pyrimidine 3.26 G. of the crude sodium salt of hydroxymethylene-cyanacetaldehyde diethylacetal are dissolved in 20 ml. of water with stirring. 4.51 G. of p-n-propylbenzamidine hydrochloride are added and the resulting solution, which reacts alkaline, is adjusted to pH 4-5 with 1 ml. of 3-N hydrochloric acid. After stirring for 5 minutes, the mixture is concentrated to dryness at 50° C. in vacuo and the residue is left to stand at room temperature with 50 ml. of acetic anhydride for 16 hours. Then, the mixture is heated to 100° C. for 1 hour, evaporated in vacuo and the residue (brown oil, partly crystalline) is taken up in methylene chloride and chromatographed on silica gel. Elution with methylene chloride and methylene chloride/2% acetone yields 5-cyano-2-(4-n-propylphenyl)-pyrimidine which is recrystallized from acetone/hexane to a constant melting point and then sublimed in a high vacuum at 120° C, whereby there are obtained colorless crystals of said pyrimidine having a melting point of 125.9°–126.0° C, which on cooling are liquid crystalline (monotropic) at 106.4° C.

The sodium salt hydroxymethylene-cyanacetaldehyde diethylacetal can be prepared as follows:

A mixture of 40.9 . of cyanacetaldehyde diethylacetal, 26.2 g. of formic acid ethyl ester and 100 ml. of absolute ether are added dropwise with stirring to a suspension of 7.4 g. of powdered sodium in 500 ml. of absolute ether. The mixture is stirred at room temperature until disappearance of the sodium (16 hours). Then, the brown precipitate formed (crude sodium salt of hydroxymethylene-cyanacetaldehyde diethylacetal) is left to settle and the supernatant solution is removed by decantation. The residue is washed by decanting twice with 200 ml. of absolute ether each time. The product is stored at 0° C. under absolute ether, since it changes on drying.

EXAMPLE 7

Preparation of 5-cyano-2-(4-n-propylphenyl)-pyrimidine

A mixture of 13.0 g. of 2-(p-n-propylphenyl)-4-chloro-5-pyrimidinecarboxylic acid ethyl ester, 1.1 g. of palladium-carbon (5%), 6.3 g. of anhydrous potassium acetate and 175 ml. of dioxane is hydrogenated at room temperature until uptake of 1 mol. of hydrogen (92 hours). The catalyst is removed by filtration, the filtrate evaporated in vacuo and any starting material present is removed by chromatography on silica gel with benzene and benzene/2% acetone as eluants. The pure, colorless 2-(p-n-propylphenyl)-5-pyrimidinecarboxylic acid ethyl ester melts at 93.5° C. after distillation in a high vacuum at 130° C. (bulb tube).

9.3 G. of 2-(p-n-propylphenyl)-5-pyrimidinecarboxylic acid ethyl ester and 21.5 ml. of ethanol are boiled under reflux with a solution of 16.0 g. of sodium hydroxide in 107 ml. of water for 1 hour. After cooling, the mixture is made congo-acidic with 82 ml. of 20% hydrochloric acid and the separated 2-(p-n-propylphenyl)-5-pyrimidinecarboxylic acid is washed with water, dried and reacted in the crude state.

8.3 G. of 2-(p-n-propylphenyl)-5-pyrimidinecarboxylic acid are boiled under reflux with 50 ml. of thionyl chloride with the exclusion of moisture for 2 hours, the excess thionyl chloride is removed in vacuo and the remaining 2-(p-n-propylphenyl)-5-pyrimidinecarboxylic acid chloride is dissolved in 100 ml. of absolute dioxane. The solution is added with stirring to a solution of 200 ml. of absolute dioxane saturated with ammonia at room temperature, a colorless precipitate forming. Then, ammonia is led into the mixture for an additional 4 hours, the mixture is allowed to stand overnight at room temperature, evaporated in vacuo and the residue stirred with 100 ml. of water for 30 minutes. The precipitate is separated, washed with water and dried. The resulting crude 2-(p-n-propylphenyl)-5-pyrimidinecarboxamide can be sublimed in a high vacuum at 170° C. for purification; melting point from 255.1° C (decomposition).

8.3 G. of 2-(p-n-propylphenyl)-5-pyrimidinecarboxamide are boiled under reflux with 100 ml. of phosphorus oxychloride with the exclusion of moisture for 2 hours. Then, the excess phosphorus oxychloride is removed in vacuo and the mixture evaporated twice with toluene in vacuo. The residue is taken up in methylene chloride and chromatographed on 100 g. of silica gel in methylene chloride. Elution with methylene chloride and methylene chloride/2% acetone yields the 5cyano-2-(4-n-propylphenyl)-pyrimidine, which is recrystallized from acetone/hexane up to a constant melting point and is sublimed at 120° C. in a high vacuum for purification. The pure, colorless 5-cyano-2-(4-n-propylphenyl)-pyrimidine has a melting point of 125.9°–126.0° C. and on cooling is liquid crystalline (monotropic) at 106.4° C. The substance is identical with the compound obtained according to Example 6.

The starting material can be obtained according to the procedure of A. R. Todd and F. Bergel, J. Chem. Soc. 1937, 366 from p-n-propylbenzamidine hydrochloride and ethoxymethylenemalonic acid diethyl ester with sodium ethylate in ethanol and subsequent treatment of the obtained 2-(p-n-propylphenyl)-4-hydroxy-5-pyrimidinecarboxylic acid ethyl ester (melting point 210.9°–211.6° C) with phosphorus oxychloride. The melting point of 2-(p-n-propylphenyl)-4-chloro-5-pyrimidinecarboxylic acid ethyl ester is 67.8°–68.2° C.

EXAMPLE 8

Preparation of 5-cyano-2-(4-n-butylphenyl)-pyrimidine

A mixture of 11.9 g. of 2-(p-n-butylphenyl)-4-chloro-5-pyrimidinecarboxylic acid ethyl ester, 1.1 g. of palladium-carbon (5%), 5.6 g. of anhydrous potassium acetate and 150 ml. of dioxane is hydrogenated at room temperature until 1 mol. of hydrogen is taken up (48 hours). After the mixture is worked up in a manner analogous to that described in Example 7, there is obtained pure, colorless 2-(p-n-butylphenyl)-5-pyrimidinecarboxylic acid ethyl ester which, after distillation in a high vacuum at 125° C., has a melting point of 86.8°–87.1° C.

9.3 G. of 2-(p-n-butylphenyl)-5-pyrimidinecarboxylic acid ethyl ester and 20 ml. of ethanol are reacted with a solution of 15.2 g. of sodium hydroxide in 100 ml. of water and worked up in a manner analogous to that described in Example 7. The dry 2-(p-n-butylphenyl)-5-pyrimidinecarboxylic acid is further reacted in the crude state.

8.3 G. of 2-(p-n-butylphenyl)-5-pyrimidinecarboxylic acid are reacted with 50 ml. of thionyl chloride with the exclusion of moisture and worked up on a manner analogous to that given in Example 7. The remaining 2-(p-n-butylphenyl)-5-pyrimidinecarboxylic acid chloride is dissolved in 100 ml. of absolute dioxane and added to a solution of 200 ml. of absolute dioxane saturated with ammonia at room temperature with stirring and further treated in a manner analogous to that described in Example 7. The obtained crude 2-(p-n-butylphenyl)-5-pyrimidinecarboxamide can be sublimed in a high vacuum at 185° C. for purification; melting point 264.0°–266.0° C.

8.2 G. of 2-(p-n-butylphenyl0-5-pyrimidinecarboxamide are reacted with 100 ml. of phosphorus oxychloride with the exclusion of moisture, worked up and purified in a manner analogous to that described in Example 7. The pure, colorless 5-cyano-2-(4-n-butylphenyl)-pyrimidine has a melting point of 108.6°–109.5° C. and on cooling is liquid crystalline (monotropic) at 101.5° C.

The starting material can be obtained according to the procedure of A. R. Todd and F. Bergel, J. Chem. Soc. 1937, 366 from p-n-butylbenzamindine hydrochloride and ethoxymethylenemalonic acid diethyl ester with sodium ethylate in ethanol and subsequent treatment of the obtained 2-(p-n-butylphenyl)-4-hydroxy-5-pyrimidinecarboxylic acid ethyl ester (melting point 198.0°–198.8° C) with phosphorus oxychloride. The melting point of 2-(p-n-butylphenyl)-4-chloro-5-pyrimidinecarboxylic acid ethyl ester is 64.9°–65.3° C.

EXAMPLE 9

Preparation of 5-cyano-2-(4-n-pentylphenyl)-pyrimdine

A mixture of 12.6 g. of 2-(p-n-pentylphenyl)-4-chloro-5-pyrimidinecarboxylic acid ethyl ester, 1.1 g. of palladium-carbon (5%), 5.6 g. of anhydrous potassium acetate and 156 ml. of ethanol is hydrogenated at room temperature until 1 mol. of hydrogen are taken up (1 hour). The mixture is worked up in a manner analogous to that described in Example 7. The pure, colorless 2-(p-n-pentylphenyl)-5-pyrimidinecarboxylic acid ethyl ester has a melting point of 85.1°–86.7° C. after distillation in a high vacuum at 130° C.

10.2 G. of 2-(p-n-pentylphenyl)-5-pyrimidinecarboxylic acid ethyl ester and 21 ml. of ethanol are reacted with a solution of 15.8 g. of sodium hydroxide in 105 ml. of water and worked up in a manner analogous to that described in Example 7. The dry 2-(p-n-pentylphenyl)-5-pyrimidinecarboxylic acid is further reacted in the crude state.

9.3 G. of 2-(p-n-pentylphenyl)-5-pyrimidinecarboxylic acid are reacted with 50 ml. of thionyl chloride with the exclusion of moisture and worked up in a manner analogous to that described in Example 7. The remaining 2-(p-n-pentylphenyl)-5-pyrimidinecarboxylic acid chloride is dissolved in 100 ml. of absolute dioxane and added with stirring to a solution of 200 ml. of absolute dioxane saturated with ammonia at room temperature and treated further in a manner analogous to that described in Example 7. The obtained, crude 2-(p-n-penthylphenyl)-5-pyrimidinecarboxamide is directly further treated.

9.1 G. of 2-(p-n-pentylphenyl)-5-pyrimidinecarboxamide are reacted with 100 ml. of phosphorus oxychloride with the exclusion of moisture, worked up and purified in a manner analogous to that described in Example 7. The pure, colorless 5-cyano-2-(4-n-pentylphenyl)-pyrimidine has a melting point of 96.0°–96.2° C. and a clearing point of 109.0° C.

The starting material can be obtained according to the procedure of A. R. Todd and F. Bergel, J. Chem. Soc. 1937, 366 from p-n-pentylbenzamide hydrochloride and ethoxymethylenemalonic acid diethyl ester with sodium ethylate in ethanol and subsequent treatment of the obtained 2-)p-n-pentylphenyl)-4-hydroxy-5-pyrimidinecarboxylic acid ethyl ester (melting point 193.9°–194.4° C) with phosphorus oxychloride. The melting point of 2-(p-n-penthylphenyl)-4-chloro-5-pyrimidinecarboxylic acid ethyl ester is 58.5°–59.2° C.

EXAMPLE 10

Preparation of 5-cyano-2-(4-n-hexylphenyl)-pyrimidine

A mixture of 15.6 g. of 2-(p-n-hexylphenyl)-4-chloro-5-pyrimidinecarboxylic acid ethyl ester, 1.3 g. of palladium-carbon (5%), 6.7 g. of anhydrous potassium acetate and 150 ml. of dioxane is hydrogenated at room temperature until 1 mol. of hydrogen is taken up (70 hours). The mixture is worked up in a manner analogous to that described in Example 7. The pure, colorless 2-(p-n-hexylphenyl)-5-pyrimidinecarboxylic acid ethyl ester has a melting point of 83.2°–83.9° C. after distillation in a high vacuum at 125° C.

14.1 G. of 2-(p-n-hexylphenyl)-5-pyrimidinecarboxylic acid ethyl ester and 28 ml. of ethanol are reacted with a solution of 20.8 g. of sodium hydroxide in 140 ml. of water and worked up in a manner analogous to that described in Exxample 7. The dry 2-(p-n-hexylphenyl)-5-pyrimidinecarboxylic acid is further reacted in the crude state.

12.0 G. of 2-(p-n-hexylphenyl)-5-pyrimidinecarboxylic acid are reacted with 80 ml. of thionyl chloride with the exclusion of moisture and worked up in a manner analogous to that described in Example 7. The remaining 2-(p-n-hexylphenyl)-5-pyrimidinecarboxylic acid chloride is dissolved in 120 ml. of abslute dioxane while warming and added with stirring to a solution of 200 ml. of absolute dioxane saturated with ammonia at room temperature and treated further in a manner analogous to that described in Example 7. A sample of the obtained crude 2-(p-n-hexylphenyl)-5-pyrimidinecarboxamide is sublimed at 180° C. in a high vacuum for purification; melting point 250.2°–258.3° C.

11.5 G. of 2-(p-n-hexylphenyl)-5-pyrimidinecarboxamide are reacted with 100 of phosphorus oxychloride with the exclusion of moisture, worked up and purified in a manner analogous to that described in Example 7. The pure, colorless 5-cyano-2-(4-n-hexylphenyl)-pyrimidine has melting point of 86.3°–87.8° C. (smectic), is nematic at 101.3° C. and has a clearing point of 102.6°–103.2° C.

The starting material can be obtained according to the procedure of A. R. Todd and F. Bergel, J. Chem. Soc. 1937, 366 from p-n-hexylbenzamide hydrochloride and ethoxymethylenemalonic acid diethyl ester with sodium ethylate in ethanol and subsequent treatment of the obtained 2-(p-n-hexylphenyl)-4-hydroxy-5-pyrimidine carboxylic acid ethyl ester (melting point 186.6°–191.0° C) with phosphorus oxychloride. The melting point of 2-(p-n-hexylphenyl)-4-chloro-5-pyrimidinecarboxylic acid ethyl ester is 59.4°–60.5° C.

EXAMPLE 11

Preparation of
5-cyano-2-(4-n-heptylphenyl)-pyrimidine

A mixture of 13.4 g. of 2-(p-n-heptylphenyl)-4-chloro-5-pyrimidinecarboxylic acid ethyl ester, 1.1 g. of palladium-carbon (5%), 5.5 g. of anhydrous potassium acetate and 155 ml. of dioxane is hydrogenated at room temperature until 1 mol. of hydrogen is taken up (68 hours). The mixture is worked up in a manner analogous to that described in Example 7. The pure, colorless 2-(p-n-heptylphenyl)-5-pyrimidinecarboxylic acid ethyl ester has a melting point of 88.8°–89.2° C. after distillation in a high vacuum at 130° C.

10.5 G. of 2-(p-n-heptylphenyl)-5-pyrimidinecarboxylic acid ethyl ester and 20 ml. of ethanol are reacted with a solution of 15.2 g.. of sodium hydroxide in 100 ml. of water and worked up in a maner analogous to that described in Example 7. The dry 2-(p-n-heptylphenyl)-5-pyrimidinecaboxylic acid is further reacted in the crude state.

9.6 G. of crude 2-(p-n-heptylphenyl)-5-pyrimidnecarboxylic acid are reacted with 50 ml. of thionyl chloride with the exclusion of moisture and worked up in a manner analogous to that described in Example 7. The remaining 2-(p-n-heptylphenyl)-5-pyrimidinecarboxylic acid chloride is dissolved in 100 ml. of absolute dioxane and added with stirring to a solution of 200 ml. of absolute dioxane saturated with ammonia at room temperature and treated further in a manner analogous to that described in Example 7. A sample of the obtained, crude 2-(p-n-heptylphenyl)-5-pyrimidinecarboxamide is sublimed in a high vacuum at 180° C. for purification; melting point 250.8°–251.5° C.

9.1 G. of 2-(p-n-heptylphenyl)-5pyrimidinecarboxamide are reacted with 100 ml. of phosphorus oxychloride with the exclusion of moisture, worked up and purified in a manner analogous to that described in Example 7. The pure, colorless 5-cyano-2-(4-n-heptylphenyl)-pyrimidine has a melting point of 96.3° C. (smectic) and a clearing point of 109.0° C.

The starting material can be obtained according to the procedure of A. B. Todd and F. Bergel, J. Chem. Soc. 1937, 366 from p-n-heptylbenzamie hydrochloride [prepared according to H. Schubert and H. Zaschke, J. prakt. Chem. 312, 494 (1970) from p-n-heptylbenzonitrile; melting point 126.0°–127.3° C[ and ethoxymethylenemalonic acid diethyl ester with sodium ethylate in ethanol and subsequent treatment of the obtained 2-(p-n-heptylphenyl)-4-hydroxy-5-primidinecarboxylic acid ethyl ester (melting point 184.7°–185.3° C) with phosphorus oxychloride. The melting point of 2(-p-n-heptylphenyl)-4-chloro-5-pyrimidinecarboxylic acid ethyl ester is 49.2°–49.8° C.

EXAMPLE 12

Preparation of
5-cyano-2-(4-n-butoxyphenyl)-pyrimidine

A mixture of 13.0 g. of 2-(p-n-butoxyphenyl)-4-chloro-5-pryrimidinecarboxylic acid ethyl ester, 1.1 g. of palladium-carbon (5%), 5.8 g. of anhydrous potassium acetate and 150 ml. of dioxane is hydrogenated at room temperature until 1 mol. of hydrogen is taken up (49 hours). The mixture is worked up in a manner analogous to that described in Example 7. The pure, colorless 2-(p-n-butoxyphenyl)-5-pyrimidinecarboxylic acid ethyl ester has a melting poit of 97.0°–99.3° C. after distillation in a high vacuum at 130° C.

10.9 G. of 2-(p-n-butoxyphenyl)-5-pyrimidinecaboxylic acid ethyl ester and 22 ml. of ethanol are reacted with a solution of 17.3 g. of sodium hydroxide in 115 ml. of water and worked up in a manner analogous to that described in Example 7. The dry 2-(p-n-butoxyphenyl)-5-pyrimidinecarboxylic acid is further reacted in the crude state.

9.6 G. of 2-)p-n-butoxyphenyld)-5-pyrimidinecaboxylic acid are reacted with 60 ml. of thionyl chloride with the exclusion of moisture and worked up in a manner analogous to that described in Example 7. The remaining 2-(p-n-butoxyphenyl)-5-pyrimidinecarboxylic acid chloride is dissolved in 100 ml. of absolute dioxane and added with stirring to a solution of 200 ml. of absolute dioxane saturated with ammonia at room temperature and treated further in a manner analogous to that described in Example 7. A sample of the obtained, crude 2-(p-n-butoxyphenyl)-5-pyrimidinecaboxamide is sublimed in a high vacuum at 180° C. for purification; melting point 266.3°–270.3° C.

9.1 G. of 2-(p-n-butoxyphenyl)-5-pyrimidinecarboxamide are reacted with 100 ml. of phosphorus oxychloride with the exclusion of moisture, worked up and purified in a manner analogous to that described in Example 7. The pure, colorless 5-cyano-2-(4-n-butoxyphenyl)-pyrimidine has a melting point of 119.1°–120.0° C. and a clearing point of 139.3° C.

The starting material can be obtained according to the procedure of A. R. Todd and F. Bergel, J. Chem. Soc. 1937, 366 from a p-n-butoxybenzamidine hydrochloride and ethoxymethylenemalonic acid diethyl ester with sodium ethylate in ethanol and subsequent treatment of the obtained 2-(p-n-butoxyphenyl)-4-hydroxy-5-pyrimidinecarboxylic acid ethyl ester (melting point 219.0°–220.0° C) with phosphorus oxychloride. The melting point of 2-(p-n-butoxyphenyl)-4-chloro-5-pyrimidinecarboxylic acid ethyl ester is 81.0°–81.5° C.

EXAMPLE 13

Preparation of
5-cyano-2-(4-n-propylphenyl)-pyrimidine 5.0 G. of 4-chloro-5-cyano-2-(4-n-propylphenyl)-pyrimidine are boiled under reflux for 1 hour while stirring in 255 ml. of 50% dioxane with 22.4 g. of zinc dust (treated with hydrochloric acid and washed with water). Then, the zinc is separated and washed with dioxane. The filtrate and washings are freed from dioxane in vacuo and the aqueous suspension is extracted with methylene chloride. The extract is dried and concentrated and the residue chromatographed on silica gel. Elution with methylene chloride and methylene chloride/2% acetone yields the 5-cyano-2-(4-n-propylphenyl)-pyrimidine, which is recrystallized from acetone/hexane up to a constant melting point and sublimed at 120° C. in a high vacuum. There are obtained colorless crystals of melting point 125.9°–126.0° C, which on cooling are liquid crystalline (monotropic) at 106.4° C. The substance is identical with the compound obtained according to Example 6.

The starting material can be obtained according to the procedure of A. R. Todd and F. Bergel, J. Chem. Soc. 1937, 365 by reaction of p-n-propylbenzamidine hydrochloride with α-ethoxymethylene- α-cyanoacetic acid ethyl ester and sodium ethylate in ethanol and then with sodium hydroxide solution. The resulting 5-cyano-4-hydroxy-2-(4-n-propylphenyl)-pyrimidine (melting point 246.0°–247.6° C) is treated with phosphorus oxychloride to give 4-chloro-5-cyano-2-(4-n-propylphenyl)-pyrimidine having a melting point of 109.4°–109.7° C.

EXAMPLE 14

Preparation of 5-cyano-2-(4-n-butylphenyl)-pyrimidine 5.2 G. of 4-chloro-5-cyano-2-(4-n-butylphenyl)-pyrimidine are reacted in 230 ml. of 50% dioxane with 21.7 g. of pre-treated zinc dust and worked up after the reaction in a manner analogous to that described in Example 13. There is obtained 5-cyano-2-(4-n-butylphenyl)-pyrimidine as colorless crystals of melting point 108.6°–109.5° C., which on cooling are nematic (monotropic) at 101.5° C. The substance is identical with the compound obtained according to Example 8.

The starting material can be obtained according to the procedure of A. R. Todd and F. Bergel, J. Chem. Soc. 1937, 365 by reaction of p-n-butylbenzamidine hydrochloride with α -ethoxymethylene- α -cyanoacetic acid ethyl ester and sodium ethylate in ethanol and then with sodium hydroxide solution. The resulting 5-cyano-4-hydroxy-2-(4-n-butylphenyl)-pyrimidine (melting point 230.3°–231.3° C) is treated with phosphorus oxychloride to give 4-chloro-5-cyano-2-(4-n-butylphenyl)-pyridine having a melting point of 106.8°–107.0° C.

EXAMPLE 15

Preparation of 5-cyano-2-(4-n-pentylphenyl)-pyrimidine 6.3 G. of 4-chloro-5-cyano-2-(4-n-pentylphenyl)-pyrimidine are reacted in 290 ml. of 50% dioxane with 25.3 g. of pre-treated zinc dust and worked up after the reaction in a manner analogous to that described in Example 13. There is obtained 5-cyano-2-(4-n-pentylphenyl)-pyrimidine as colorless crystals having a melting point of 96.0°–96.2° C. and clearing point of 109.0° C. The substance is identical with the compound obtained according to Example The starting material can be obtained according to the procedure of A. R. Todd and F. Bergel, J. Chem. Soc. 1937, 365 by reaction of p-n-pentylbenzamidine hydrochloride with α-ethoxymethylene- α -cyanoacetic acid ethyl ester and sodium ethylate in ethanol and then with sodium hydroxide solution. The resulting 5-cyano-4-hydroxy-2-(4-n-pentylphenyl)-pyrimidine (melting point 199°–205° C) is treated with phosphorus oxychaloride to give 4-chloro-5-cyano-2-(4-n-pentylphenyl)-pyrimidine having a melting point of 96.0°–96.3° C.

EXAMPLE 16

Preparation of 5-cyano-2-(4-n-hexylphenyl)-pyrimidine 5.7 G. of 4-chloro-5-cyano-2-(4-n-hexylphenyl)-pyrimidine are reacted in 250 ml. of 50% dioxane with 21.9 g. of pre-treated zinc dust and worked up after the reaction in a manner analogous to that described in Example 13. There is obtained 5-cyano-2-(4-n-hexylphenyl)-pyrimidine as colorless crystals having a melting point of 86.3°–87.8° C. (smectic); nematic at 101.3° C; clearing point 102.6°–103.2° c. The substance is identical with the compound obtained according to Example 10.

The starting material can be obtained according to the procedure of A. R. Todd and F. Bergel, J. Chem. Soc. 1937, 365 by reaction of p-n-hexylbenzamidine hydrochloride with α-ethoxymethylene- α-cyanoacetic acid ethyl ester and sodium ethylate in ethanol and then with sodium hydroxide solution. The resulting 5-cyano-4-hydroxy-2-(4-n-hexylphenyl)-pyrimidine (melting point 204.4°–205.2° C) is treated with phosphorus oxychloride to give 4-chloro-5-cyano-2-(4n-hexylphenyl)-pyrimidine having a melting point of 80.3°–80.5° C.

EXAMPLE 17

Preparation of 5-cyano-2-(4-n-heptylphenyl)-pyrimidine 5.2 G. of 4-chloro-5-cyano-2-(4-n-heptylphenyl)-pyrimidine are reacted in 220 ml. of 50% dioxane with 19.3 g. of pre-treated zinc dust and worked up after the reaction in a manner analogous to that described in Example 13. There is obtained 5-cyano-2-(4-n-heptylphenyl)-pyrimidine having a melting point of 96.3° C. (smectic) and clearing point 109.0° C. The substance is identical with the compound obtained according to Example 11.

The starting material can be obtained according to the procedure of A. R. Todd and F. Bergel, J. Chem. Soc. 1937, 365 by reaction of p-n-heptylbenzamidine hydrochloride with α-ethoxymethylene- α-cyanoacetic acid ethyl ester and sodium ethylate in ethanol and then with sodium hydroxide solution. The resulting 5-cyano-4-hydroxy-2-(4-n-heptylphenyl)-pyrimidine (melting point 195.6°–198.6° C) is treated with phosphorus oxychloride to give 4-chloro-5-cyano-2-(4-n-heptylphenyl)-pyrimidine having a melting point of 76.3°–76.8° C.

EXAMPLE 18

Preparation of 5-cyano-2-(4-ethoxyphenyl)-pyrimidine 5.0 G. of 4-chloro-5-cyano-2-(4-ethoxyphenyl)-pyrimidine are reacted in 250 ml. of 50% dioxane with 22.2 g. of pre-treated zinc dust and worked up after the reaction in a manner analogous to that described in Example 13. There is obtained 5-cyano-2-(4-ethoxyphenyl)-pyrimidine as colorless crystals having a melting point of 152.6°–153.0° C. which on cooling are nematic (mono-tropic) at 149.7° C.

The starting material can be obtained according to the procedure of A. R. Todd and F. Bergel, J. Chem. Soc. 1937, 365 by reaction of p-ethoxybenzamidine hydrochloride with α-ethoxymethylene- α-cyanoacetic acid ethyl ester and sodium ethylate in ethanol and then with sodium hydroxide solution. The resulting 5-cyano-4-hydroxy-2-(4-ethoxyphenyl)-pyrimidine (melting point 288.6°–290.5° C) is treated with phosphorus oxychloride to give 4-chloro-5-cyano-2-(4-ethoxyphenyl)-pyrimidine having a melting point of 190.6°–192.4° C.

EXAMPLE 19

Preparation of
5-cyano-2-(4-n-propoxyphenyl)-pyrimidine 4.7 G. of 4-chloro-5-cyano-2-(4-n-propoxyphenyl)-pyrimidine are reacted in 230 ml. of 50% dioxane with 20.0 g. of pre-treated zinc dust and worked up after the reaction in a manner analogous to that described in Example 13. There is obtained 5-cyano-2-(4-n-propoxyphenyl)-pyrimidine as colorless crystals having a melting point of 146.2°–146.6° C, which on cooling are nematic (monotropic) at 137.0° C.

The starting material can be obtained according to the procedure of A. R. Todd and F. Bergel, J. Chem. Soc. 1937, 365 by reaction of p-n-propoxybenzamidine hydrochloride with α-ethoxymethylene-α-cyanoacetic acid ethyl ester and sodium ethylate in ethanol and then with sodium hydroxide solution. The resulting 5-cyano-4-hydroxy-2-(4-n-propoxyphenyl)-pyrimidine (melting point 255.3°–256.5° C) is treated with phosphorus oxychloride to give 4-chloro-5-cyano-2-(4-n-propoxyphenyl)-pyrimidine having a melting point of 193.3°–194.4° C.

EXAMPLE 20

Preparation of
5-cyano-2-(4-n-butoxyphenyl)-pyrimidine 4.1 G. of 4-chloro-5-cyano-2-(4-n-butoxyphenyl)-pyrimidine are reacted in 190 ml. of 50% dioxane with 16.4 g. of pre-treated zinc dust and worked up after the reaction in a manner analogous to that described in Example 13. There is obtained pure, colorless 5-cyano-2-(4-n-butoxyphenyl)-pyrimidine having a melting point of 119.1°–120.0° C. and a clearing point of 139.3° C. The substance is identical with the compound obtained according to Example 12.

The starting material can be obtained according to the procedure of A. R. Todd and F. Bergel, J. Chem. Soc. 1937, 365 by reaction of p-n-butoxybenzamidine hydrochloride with α-ethoxymethylene-α-cyanoacetic acid ethyl ester and sodium ethylate in ethanol and then with sodium hydroxide solution. The resulting 5-cyano-4-hydroxy-2(4-n-butoxyphenyl)-pyrimidine (melting point 223.2°–229.5° C) is treated with phosphorus oxychloride to give 4-chloro-5-cyano-2-(4-n-butoxyphenyl)-pyrimidine having a melting point of 169.7°–170.2° C.

EXAMPLE 21

Preparation of
5-cyano-2-(4-n-pentyloxyphenyl)-pyrimidine 6.0 G. of 4-chloro-5-cyano-2-(4-n-pentyloxyphenyl)-pyrimidine are reacted in 260 ml. of 50% dioxane with 23.0 g. of pre-treated zinc dust and worked up after the reaction in a manner analogous to that described in Example 13. There is obtained 5-cyano-2-(4-n-pentyloxyphenyl)-pyrimidine as colorless crystals having a melting point of 98.0°–98.1° C. (smectic); nematic at 102.1° C; clearing point 133.2° C.

The starting material can be obtained according to the procedure of A. R. Todd and F. Bergel, J. Chem. Soc. 1937, 365 by reaction of p-n-pentyloxybenzamidine hydrochloride with α-ethoxymethylene-α-cyanoacetic acid ethyl ester and sodium ethylate in ethanol and then with sodium hydroxide solution. The resulting 5-cyano-4-hydroxy-2-(4-n-pentyloxyphenyl)-pyrimidine (melting point 213.5°–215.5° C) is treated with phosphorus oxychloride to give 4-chloro-5-cyano-2-(4-n-pentyloxyphenyl)-pyrimidine having a melting point of 140.5°–142.0° C.

EXAMPLE 22

Preparation of
5-cyano-2-(4-n-hexyloxyphenyl)-pyrimidine 3.0 G. of 4-chloro-5-cyano-2-(4-n-hexyloxyphenyl)-pyrimidine are reacted in 125 ml. of 50% dioxane with 11.0 g. of pre-treated zinc dust and worked up after the reaction in manner analogous to that described in Example 13. There is obtained 5-cyano-2-(4-n-hexyloxyphenyl)-pyrimidine as colorless crystals having a melting point of 93.5°–93.8° C. (smectic); nematic at 121.2° C; clearing point 134.0° C.

The starting material can be obtained according to the procedure of A. R. Todd and F. Bergel, J. Chem. Soc. 1937, 365 by reaction of p-n-hexyloxybenzamidine hydrochloride with α-ethoxymethylene-α-cyanoacetic acid ethyl ester and sodium ethylate in ethanol and then with sodium hydroxide solution. The resulting 5-cyano-4-hydroxy-2-(4-n-hexyloxyphenyl)-pyrimidine (melting point 193.0° C; smectic up to 226.0° (clearing point)) is treated with phosphorus oxychloride to give 4-chloro-5-cyano-2-(4-n-hexyloxyphenyl)-pyrimidine having a melting point of 132.7°–133.1° C.

EXAMPLE 23

Preparation of
5-cyano-2-(4-n-heptyloxyphenyl)-pyrimidine 6.3 G. of 4-chloro-5-cyano-2-(4n-heptyloxyphenyl)-pyrimidine are reacted in 275 ml. of 50% dioxane with 23.9 g. of pre-treated zinc dust and worked up after the reaction in a manner analogous to that described in Example 13. There is obtained 5-cyano-2-(4-n-heptyloxyphenyl)-pyrimidine as colorless crystals having a melting point of 102.4° C. (smectic); nematic at 126.9° C; clearing point at 129.5° C.

The starting material can be obtained according to the procedure of A. R. Todd and F. Bergel, J. Chem. Soc. 1937, 365 by reaction of p-n-heptyloxybenzamidine hydrochloride with α-ethoxymethylene-α-cyanoacetic acid ethyl ester and sodium ethylate in ethanol and then with sodium hydroxide solution. The resulting 5-cyano-4-hydroxy-2-(4-n-heptyloxyphenyl)-pyrimidine (melting point 180.8° C; smectic up to 231.5° C. (clearing point) is treated with phosphorus oxychloride to give 4-chloro-5-cyano-2-(4-n-heptyloxyphenyl)-pyrimidine having a melting point of 133.3°–134.6° C.

EXAMPLE 24

Preparation of p-n-hexylcinnamic acid p'-cyanophenyl ester

Crude p-n-hexylcinnamic acid chloride, obtained by boiling 5.3 g. of p-n-hexylcinnamic acid with thionyl chloride, is dissolved in 35 ml. of absolute benzene and added to 2.9 g. of p-hydroxybenzonitrile in 40 ml. of absolute pyridine. The mixture is then heated at 50° C. overnight. The mixture is poured on to ice water and extracted 3 times with ether. The combined organic phases are washed with dilute hydrochloric acid. Unreacted starting materials are separated with dilute sodium hydroxide and the ester solution is washed neutral. The crude product is recrystallized from hexane several times and there is obtained pure p-n-hexylcinnamic acid p'-cyanophenyl ester having a melting point of 71.5° C; clearing point 106.5° C.

The starting material can be prepared as follows:

9.4 G. of p-n-hexylbenzaldehyde in 5 ml. of absolute pyridine are treated with 5.15 g. of malonic acid and 5 drops of piperidine. The mixture is then heated at 100° C. for 11 hours, subsequently poured on to cold aqueous hydrochloric acid and extracted with ether. The p-n-hexylcinnamic acid obtained after recrystallization of the crude product from hexane/ether has a melting point of 107°-109° C.

EXAMPLE 25

Preparation of p-[N-(p-cyanophenyl)-formidoyl]-phenyl-methyl carbonate

A mixture of 6.1 g. of p-formylphenyl-carbonic acid methyl ester and 4.0 g. of p-aminobenzonitrile in 100 ml. of benzene is gasssed with argon and heated under reflux for 1 hour (bath temperature 135°C). The resulting water is separated with a water separator. The benzene condensing in the reflux condenser is led back into the reaction vessel for a further hour through a layer of 100 g. of aluminum oxide (Activity I). After cooling, the mixture is freed from the solvent in vacuo at 50° C. (bath temperature). There are obtained 9.3 g. of almost colorless crystals which are recrystallized several times from isopropanol up to a constant melting point and clearing point and until by-products disappear in the gas chromatogram. The resulting pure, colorless p-[N-(p-cyanophenyl)-formidoyl]-phenyl-methyl carbonate has a melting point of 139.0°-139.2° C. and a clearing point of 156.0° C. UV (ethanol): $\epsilon_{274}$ = 2400 (shoulders at 315 and 234 nm; minima at 242 nm).

EXAMPLE 26

Preparation of p-[(p-cyanobenzylidene)amino]phenyl-methyl carbonate

A mixture of 0.835 g. of p-methoxycarbonyloxyaniline and 0.655 g. of p-cyanobenzaldehyde in 50 ml. of benzene is gassed with argon and heated under reflux for 1 hour (bath temperature 130° C). The resulting water is separated with a water separator. The benzene condensing in the reflux condenser is led back into the reaction vessel or a further hour through a layer of 20 g. of aluminum oxide (Activity I). After cooling, the mixture is freed from solvent in vacuo at 50° C. (bath temperatue). There are obtained 1.395 g. of yellowish crystals which are recrystallized several times from isopropanol up to a constant melting point and clearing point and until by-products disappear in the gas chromatogram. The resulting, pure, slightly yellowish p-[(p-cyanobenzylidene)amino]phenyl-methyl carbonate has a melting point of 145.1°-146.2° C. and a clearing point of 163.4° C. UV (ethanol): $\epsilon_{270}$ = 20250, $\epsilon_{324}$ = 10800 (shoulders at 243 and 221 nm; minima at 312 and 233 nm).

EXAMPLE 27

Preparation of p-[(p-cyano-phenoxy)carbonyl]phenyl-ethyl carbonate 5.66 G. of p-cyanophenol are dissolved in 66 ml. of absolute pyridine and cooled to −10° C. while stirring. In the course of 10 minutes, there is added portionwise thereto a total of 8.6 g. of crude p-carbethoxy-oxybenzoyl chloride. The temperature rises to 0° C. and pyridine hydrochloride precipitates out. The mixture is subsequently stirred overnight at room temperature and the suspension is poured on to a mixture of 200 ml. of ice and 200 ml. of 20% hydrochloric acid. The mixture is extracted three times with ethyl acetate, washed with water, dried over sodium sulfate and evaporated in vacuo. The 12.4 g. of reddish crystals obtained as the residue are dissolved in benzene and chromatographed on 400 g. of silica gel. Elution with benzene/1% acetone (v/v) yields 8.1 g. of yellowish crystals which are recrystallized from acetone/hexane up to a constant melting point and clearing point. The resulting, pure p-[(p-cyanophenoxy)carbonyl]phenyl-ethyl carbonate melts at 144.7°-144.8° C. and, with cooling, is liquid crystalline (monotropic) at 115.8° C. UV (ethanol): $\epsilon_{241}$ = 29700.

The starting material is prepared as follows:

Chloroformic acid ethyl ester is allowed to act on p-hydroxybenzoic acid in the presence of IN sodium hydroxide according to the method described by E. Fischer, Ber. 41, 2877 (1908). There is obtained crystalline p-carbethoxy-oxybenzoic acid which is treated with thionyl chloride according to the procedure described by H. Schonenberger et al., Arzneimittelforschung, 14, 324 (1964). After removal of the excess thionyl chloride in vacuo there is obtained crude p-carbethoxy-oxybenzoyl chloride which is used directly in the procedure described in the first paragraph of this Example.

EXAMPLE 28

Preparation of 4'-cyano-4-biphenylyl butyrate 0.390 G. of 4'-cyano-4-hydroxy-biphenyl are dissolved in 4.0 ml. of absolute pyridine and cooled to −10° C. while stirring. In the course of 2 minutes, 0.255 g. of butyric acid chloride are added dropwise thereto. The temperature rises to 0° C. and pyridine hydrochloride precipitates out. Subsequently, the mixture is stirred overnight at room temperature and the suspension is poured on to a mixture of 12 g. of ice and 12 ml. of 20% hydrochloric acid. The mixture is extraced three times with ethyl acetate, washed with water, dried over sodium sulfate and evaporated in vacuo. The 0.552 g. of yellowish crystals obtained as the residue are dissolved in benzene and chromatographed on 40 g. of silica gel. Elution with benzene yields 0.521 g. of yellowish crystals which are recrystallized from acetone/hexane up to a constant melting point and clearing point. The resulting, pure 4'-cyano-4-biphenylyl butyrate melts at 77.9°-78.2° C. and on cooling is liquid crystalline (monotropic) at 74.7° C. UV (ethanol): $\epsilon_{272}$ = 26100.

We claim:

1. A nematic mixture for electro-optical purposes which comprises two or more compounds of the formula

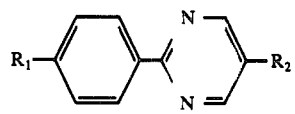

wherein one of $R_1$ and $R_2$ is cyano and the other is straight-chain alkyl of 3 to 9 carbon atoms, straight-chain alkoxy of 2 to 9 carbon atoms or straight-chain alkanoyloxy of 2 to 9 carbon atoms.

2. A nematic mixture for electro-optical purposes which comprises one or more compounds of the formula

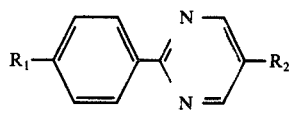

wherein one of $R_1$ and $R_2$ is cyano and the other is straight-chain alkyl of 3 to 9 carbon atoms, straight-chain alkoxy of 2 to 9 cabon atoms or straight-chain alkanoyloxy of 2 to 9 carbon atoms,
and one or more nematic substances.

3. A nematic mixture in accordance with claim 2 which comprises a compound of the formula

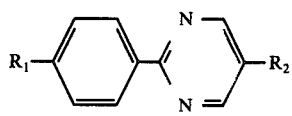

wherein one of $R_1$ and $R_2$ is cyano and the other is straight-chain alkyl of 3 to 9 carbon atoms, straight-chain alkoxy of 2 to 9 carbon atoms or straight-chain alkanoyloxy of 2 to 9 carbon atoms,
or mixtures thereof and a compound of the formula

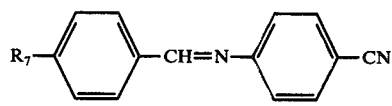

wherein $R_7$ is straight-chain alkyl of 2 to 8 carbon atoms, straight-chain alkoxy of 4 to 7 carbon atoms, straight-chain alkanoyloxy of 2 to 8 carbon atoms or straght-chain alkylcarbonate of 2 to 11 carbon atoms,
or mixtures thereof.

4. A nematic mixture in accordance with claim 2 which comprises a compound of the formula

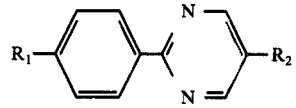

wherein one of $R_1$ and $R_2$ is cyano and the other is straight-chain alkyl of 3 to 9 carbon atoms, straight-chain alkoxy of 2 to 9 carbon atoms or straight-chain alkanoyloxy of 2 to straight-chain 9 carbon atoms,
or mixtures thereof and a compound of the formula

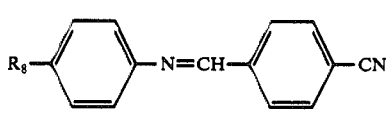

wherein $R_8$ is straight-chain alkyl of 4 to 7 carbon atoms or straight-chain alkylcarbonate of 2 to 11 carbon atoms,
or mixtures thereof.

5. A nematic mixture in accordance with claim 2 which comprises a compound of the formula

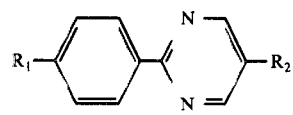

wherein one of $R_1$ and $R_2$ is cyano and the other is straight-chain alkyl of 3 to 9 carbon atoms, straight-chain alkoxy of 2 to 9 carbon atoms or straight-chain alkanoyloxy of 2 to 9 carbon atoms,
or mixtures thereof and a compound of the formula

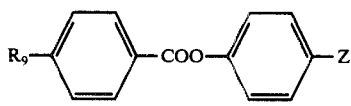

wherein Z is cyano and $R_9$ is straight-chain alkyl of 4 to 8 carbon atoms, straight-chain alkoxy of 5 to 8 carbon atoms, straight-chain alkanoyloxy of 2 to 8 carbon atoms or straight-chain alkylcarbonate of 3 to 11 carbon atoms,
or mixtures thereof.

6. A nematic mixture in accordance with claim 2 which comprises a compound of the formula

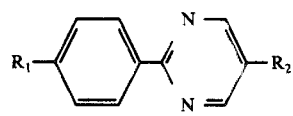

wherein one of $R_1$ and $R_2$ is cyano and the other is straight-chain alkyl of 3 to 9 carbon atoms, straight-chain alkoxy of 2 to 9 carbon atoms or straight-chain alkanoyloxy of 2 to 9 carbon atoms,
or mixtures thereof and a compound of the formula

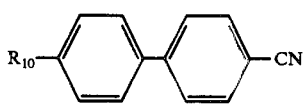

wherein $R_{10}$ is straight-chain alkyl of 5 to 7 carbon atoms straight-chain alkoxy of 5 to 7 carbon atoms, straight-chain alkanoyloxy of 4 to 9 carbon atoms or straight-chain alkylcarbonate of 4 to 11 carbon atoms,
or mixtures thereof.

7. A nematic mixture in accordance with claim 2 which comprises a compound of the formula

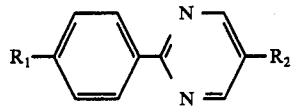

wherein one of R₁ and R₂ is cyano and the other is straight-chain alkyl of 3 to 9 carbon atoms, straight-chain alkoxy of 2 to 9 carbon atoms or straight-chain alkanoyloxy of 2 to 9 carbon atoms,
or mixtures thereof and a compound of the formula

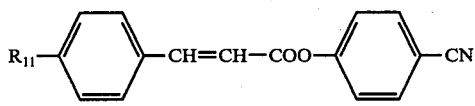

wherein $R_{11}$ is straight-chain alkyl of 1 to 8 carbon atoms, or mixtures thereof.

8. A nematic mixture in accordance with claim 2 which comprises a compound of the formula

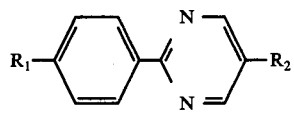

wherein one of R₁ and R₂ is cyano and the other is straight-chain alkyl of 3 to 9 carbon atoms, straight-chain alkoxy of 2 to 9 carbon atoms or straight-chain alkanoyloxy of 2 to 9 carbon atoms,
or mixtures thereof and a compound of the formula

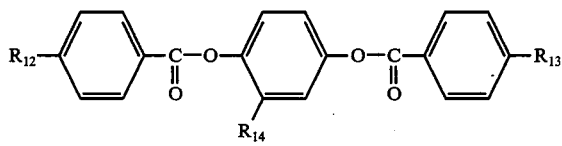

wherein $R_{12}$ and $R_{13}$ each are straight-chain alkyl of 1 to 10 carbon atoms, straight-chain alkoxy of 1 to 10 carbon atoms, straight-chain alkanoyloxy of 2 to 11 carbon atoms or straight-chain alkylcarbonate of 2 to 11 carbon atoms and $R_{14}$ is chlorine, bromine, methyl, acetyl or methoxycarbonyl,
or mixtures thereof.

9. A nemantic mixture in accordance with claim 2 which comprises 5-n-pentyl-2-(4-cyanophenyl)-pyrimidine, p-n-hexylbenzoic acid p'-cyanophenyl ester and p-n-octylbenzoic acid p'-cyanophenyl ester.

10. A nemantic mixture in accordance with claim 2 which comprises 5-n-hexyl-2-(4-cyanophenyl)-pyrimidine, p-n-hexylbenzoic acid p'-cyanophenyl ester and p-n-octylbenzoic acid p'-cyanophenyl ester.

11. A nematic mixture in accordance with claim 2 which comprises 5-n-hexyl-2-(4-cyanophenyl)-pyrimidine, 4'-n-heptyl-4-cyanobiphenyl and 4'-n-penyl-4-cyanobiphenyl.

12. A nematic mixture in accordance with claim 1 which comprises 5-n-pentyl-2-(4-cyanophenyl)-pyrimidine and 5-n-heptyl-2-(4-cyanophenyl)-pyrimidine.

13. A nematic mixture in accordance with claim 2 which comprises 5-n-heptyl-2-(-cyanophenyl)-pyrimidine, -cyanophenyl)-pyrimidine, p-n-hexanoyloxybenzoic acid p'-ethoxyphenyl ester, p-n-hexylbenzoic acid p'-cyanophenyl ester and p-n-octylbenzoic acid p'-cyanophenyl ester.

14. A nematic mixture in accordance with claim 2 which comprises 5-n-heptyl-2-(4-yanophenyl)-pyrimidine, p-n-hexylbenzoic acid p'-cyanophenyl ester, p-n-octylbenzoic acid p'-cyanophenyl ester and methylhydroquinone di-(p-n-butylbenzoate).

15. A nematic mixture in accordance with claim 2 which comprises 5-n-heptyl-2-(4-cyanophenyl)-pyrimidine, 5-n-pentyl-2-(4-cyanophenyl)-pyrimidine and 4'-n-heptyl-4-cyanobiphenyl.

16. A nematic mixture in accordance withh claim 2 which comprises 4'-n-pentyl-4-cyanobiphenyl, 4'-n-heptyl-4-cyanobiphenyl and 5-cyano-2-(4-n-butyloxyphenyl)-pyrimidine.

17. A nematic mixture in accordance with claim 2 which comprises 4'-n-pentyl-4-cyanobiphenyl, 4'-n-heptyl-4-cyanobiphenyl and 5-cyano-2-(4-n-pentylphenyl)-pyrimidine.

18. A nematic mixture in accordance with claim 2 which comprises 4'-n-pentyl-4-cyanobiphenyl, 4'-n-heptyl-4-cyanobiphenyl and 5-cyano-2-(4-n-hexylphenyl)-pyrimidine.

19. A nematic mixture in accordance with claim 2 which comprises 4'-n-pentyl-4-cyanobiphenyl, 4'-n-heptyl-4-cyanobiphenyl, 5-cyano-2-(4-n-pentyloxyphenyl)-pyrimidine and 5-cyano-2-(4-n-hexylphenyl)-pyrimidine.

20. A nematic mixture in accordance with claim 2 which comprises 4'-n-pentyl-4-cyanobiphenyl, 4'-n-heptyl-4-cyanobiphenyl, 5-cyano-2-(4-n-butylphenyl)-pyrimidine, 5-cyano-2-(4-n-pentylphenyl)-pyrimidine and 5-cyano-2-(4-n-hexylphenyl)-pyrimidine.

21. A nematic mixture in accordance with claim 2 which comprises 4'-n-pentyl-4-cyanobiphenyl, 4'-n-heptyl-4-cyanobiphenyl, 5-cyano-2-(4-n-butylphenyl)-pyrimidine, 5-cyano-2-(4-n-hexylphenyl)-pyrimidine and 5-cyano-2-(4-n-pentyloxyphenyl)-pyrimidine.

22. A nematic mixture in accordance with claim 2 which comprises 4'-n-pentyl-4-cyanobiophenyl, 4'-n-heptyl-4-cyanobiphenyl, 4'-n-heptyloxy-4-cyanobiphenyl, 4'-n-octyloxy-4-cyanobiphenyl, 5-cyano-2-(4-n-pentylphenyl)-pyrimidine and 5-cyano-2-(4-n-butyloxyphenyl)-pyrimidine.

23. A nematic mixture in accordance with claim 2 which comprises p-[(p-n-propylbenzylidene)amino]-benzonitrile, p-[(p-n-butylbenzylidene)amino]-benzonitrile, p-[(p-n-hexylbenzylidene)amino]-benzonitrile, 5-cyano-2-(4-n-propylphenyl)-pyrimidine, 5-cyano-2-(4-n-butylphenyl)-pyrimidine, 5-cyano-2-(4-n-pentylphenyl)-pyrimidine, 5-cyano-2-(4-n-hexylphenyl)-pyrimidine and 5-cyano-2-(4-n-heptylphenyl)-pyridine.

24. An optical cell comprising a liquid crystal means comprising one or more compounds selected from the group consisting of compounds of the formula

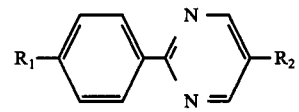

wherein one of R₁ and R₂ is cyano and the other is straight-chain alkyl of 3 to 9 carbon atoms, straight-chain alkoxy of 2 to 9 carbon atoms or straight-chain alkanoyloxy of 2 to 9 carbon atoms,
in the liquid crystalline state disposed between two plate means at least one of which plate means is transparent; means for controlling the optical activity of the cell; and said liquid crystal means having a helical structure in the direction perpendicular to the plate means and the surfaces of the plate means being wall oriented.

25. An optical cell comprising a liquid crystal means comprising one or more compounds selected from the group consisting of compounds of the formula

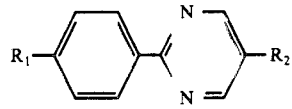

wherein one of $R_1$ and $R_2$ is cyano and the other is straight-chain alkyl of 3 to 9 carbon atoms, straight-chain alkoxy of 2 to 9 carbon atoms or straight-chain alkanoyloxy of 2 to 9 carbon atoms, in the liquid crystalline state, and one or more nematic substances disposed between two plate means at least one of which plate means is transparent; means for controlling the optical activity of the cell; and said liquid crystal means having a helical structure in the direction perpendicular to the plate means and the surfaces of the plate means being wall oriented.

* * * * *

UNITED STATES PATENT AND TRADEMARK OFFICE
CERTIFICATE OF CORRECTION

PATENT NO. : 4,066,570
DATED : January 3, 1978
INVENTOR(S) : Arthur Boller et al.

It is certified that error appears in the above-identified patent and that said Letters Patent are hereby corrected as shown below:

Column 27, claim 3, line 52, "straght-chain" should be:
　　　　straight-chain

Column 27, claim 4, line 66, "of 2 to straight-chain 9 carbon atoms," should be:
　　　　of 2 to 9 carbon atoms, Column 29, claim 10, line 54, "A nemantic" should be:
　　　　A nematic Column 29, claim 11, line 60, "4'-n-penyl-" should be:
　　　　4'-n-pentyl- Column 29, claim 13, line 66, "2-(-cyanophenyl)-" should be:
　　　　2-(4-cyanophenyl)-

Column 29, claim 13, line 67, delete "-cyanophenyl)-pyrimidine,"

Column 30, claim 14, line 4, "2-(4-yanophenyl)-" should be:
　　　　2-(4-cyanophenyl)-

UNITED STATES PATENT OFFICE
CERTIFICATE OF CORRECTION

Patent No. 4,066,570         Dated January 3, 1978

Inventor(s) Arthur Boller et al.

It is certified that error appears in the above-identified patent and that said Letters Patent are hereby corrected as shown below:

Column 30, claim 19, line 24, "A nemantic" should -- A nematic --.

Signed and Sealed this

*Thirteenth* Day of *March 1979*

[SEAL]

Attest:

RUTH C. MASON
*Attesting Officer*

DONALD W. BANNER
*Commissioner of Patents and Trademarks*